Figure 1:
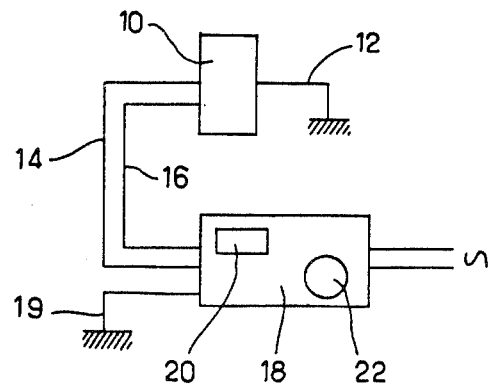

United States Patent [19]

Brun et al.

[11] Patent Number: 4,546,312

[45] Date of Patent: Oct. 8, 1985

[54] CELL FOR THE MEASUREMENT OF THE DIELECTRIC CONSTANT OF VISCOUS OR PASTY SUBSTANCES

[75] Inventors: Alain M. Brun, Paris; Louis Marcotte, Chevilly La Rue Rungis; Myriam Mellul, Vitry-Sur-Seine, all of France

[73] Assignee: L'Oreal, Paris, France

[21] Appl. No.: 472,247

[22] Filed: Mar. 4, 1983

[30] Foreign Application Priority Data

Mar. 4, 1982 [FR] France .................... 82 03606

[51] Int. Cl.$^4$ ............................ G01R 27/26
[52] U.S. Cl. .................... 324/61 P; 324/65 P
[58] Field of Search ............ 324/71.1, 61 P, 61 R, 324/65 P

[56] References Cited

U.S. PATENT DOCUMENTS

| 2,830,266 | 4/1958 | Southwick | 324/65 P |
| 2,904,751 | 9/1959 | Parsons | 324/61 P |
| 3,939,409 | 2/1976 | Hogg | 324/71.1 |

FOREIGN PATENT DOCUMENTS

| 459846 | 4/1928 | Fed. Rep. of Germany . |
| 2358307 | 5/1975 | Fed. Rep. of Germany . |

OTHER PUBLICATIONS

"Cryogenics", Sep. 1981, Electrocalorimetric apparatus for measuring losses in superconducting samples, by Ph. Dubernet and T. Pech.
"Review of Scientific Instruments:" vol. 51, Jul. 1980, Capacitance Cell for Liquids, by D. T. Jacobs, S. C. Greer, French Search Report, FR 82 03 606, Oct. 1, 1982.

*Primary Examiner*—Stanley T. Krawczewicz
*Assistant Examiner*—Jose M. Solis
*Attorney, Agent, or Firm*—Cushman, Darby & Cushman

[57] ABSTRACT

A cell for the measurement of the dielectric properties of liquids, pastes or flowable solids (i.e. solids whose melting temperatures are low enough to allow them to be poured into the cell) comprises a bullet-shaped internal electrode having its cylindrical portion in register with a surrounding coaxial cylindrical external electrode which is extended at each end by electrically conductive annular guard members insulated from the external electrode by means of spacers of electrically insulating material.

The internal electrode is mounted coaxially within the external electrode by means of a tapered male-female centering connector whose male and female elements are both connected to earth.

11 Claims, 2 Drawing Figures

CELL FOR THE MEASUREMENT OF THE DIELECTRIC CONSTANT OF VISCOUS OR PASTY SUBSTANCES

DESCRIPTION

The present invention concerns the measurement of the electric properties of viscous or pasty substances and more particularly, a cell for the measurement of the dielectric constant of liquid, pasty and even solid substances when the melting temperature is relatively low and allows the substance to be poured into the cell.

Although it is stated that the cell is intended for the measurement of the dielectric constant, it also allows the dissipation factor, the permittivity and the angle of loss of the tested material to be determined in the conventional way.

The dielectric constant of liquids is usually measured in cells having two flat electrodes, usually disc shaped ones forming capacitor electrodes, between which the liquid examined constitutes the dielectric. Such measurements may be utilised in very wide frequency ranges, for instance, up to $10^9$ Hz and with great accuracy, particularly when the electrodes are provided with guard rings. It is known that these guard rings are devices which geometrically extend the electrodes but are electrically insulated therefrom so that the electric field lines at the edge of the electrodes should not be disturbed; the edge effects which produce a curving of the field lines appear substantially only on the guard rings. Since the measurement is only effected with flat, guarded electrodes, the disturbances due to the edge effects are eliminated.

Cells of the above mentioned type are perfectly satisfactory in the case of liquids and have the advantage of allowing the thickness of the dielectric to be varied. However, they are not suitable in the case of viscous liquids or of pastes. Cleaning of the electrodes necessitates a complete dismantling of the apparatus and setting it up again. This latter operation is very delicate since it concerns numerous elements and since these latter have to be repositioned with great accuracy. For this reason, this type of cell is not used for measuring the electric parameters of viscous liquids or of pastes.

A known cell for the measurement of the dielectric constant of viscous liquids and of pastes comprises two coaxial cylindrical electrodes of which the internal electrode ends in a pointed tip; the internal electrode is carried by an insulating device and is connected to a central terminal. The internal electrode and its central terminal are not in contact with the conducting base frame of the cell, which base frame is connected to a second terminal surrounding the central terminal; an external cylindrical electrode is fitted on the said base frame.

This cell has advantages because cleaning and dismantling are very simple. It comprises only two elements which can be fitted one on the other or be separate. Filling, even with very pasty substances, is easy without any bubbles remaining which would be liable to disturb the measurement. Yet this cell has significant drawbacks. First, the pointed tip of the central electrode creates very important edge effects which interfere with the measurements obtained. Then the electric contact between the external electrode and the corresponding terminal which is carried by the base frame is effected by means of fitting two elements which may be separated from the cell. When some substance remains between the base frame and the external electrode, the electric measurement is disturbed so much so that the results are not reliable.

Thus the drawbacks of this known cell are, on the one hand, the fact that the measurement is interfered with by the edge effects and, secondly, the fact that the closing of the measurement circuit requires a good contact between metal components between which there may remain a film of the dielectric substance to be measured.

The invention concerns a cell for the measurement of the electric properties of viscous or pasty substances whose results are not vitiated by the edge effects; more particularly, according to the invention, a cell of a cylindrical type is not subject to any measurement interference by the edge effects because at least one electrode is provided with guard rings.

Accordingly the present invention provides a cell for the measurement of the dielectric properties of a viscous or pasty substance, such cell comprising: two separable elements, the first of which elements has an outer cylindrical electrically conductive surface and is intended to form an internal electrode connected to a first terminal, and the second of which elements has an inner cylindrical electrically conductive surface and is intended to form an external electrode which is connected to a second terminal; and a centering device comprising a frustoconical male element formed on the first element and coaxial with the internal electrode and a frustoconical recess formed in the second element and coaxial with the external electrode for keeping said two separable elements in cooperation with each other in an operating position wherein the two cylindrical conductive surfaces are substantially coaxial and are at least partly disposed opposite each other; wherein the inner cylindrical surface of the external electrode is extended at each one of its ends by an electrically insulating surface followed by an electrically conductive surface, the conductive surfaces of the extension being insulated in relation to the external electrode but being connected together and to a third terminal.

The measurement circuit does not require the passing of the measurement current between disconnectable conducting elements. Finally, it concerns a measurement cell wherein the electrodes are centred automatically in a reproducible manner; the centering is automatically ensured by a male frustoconical element which is fitted in a complementary frustoconical housing.

The centering device does not ensure the transmission of the measurement current. The male element and/or the female element or recess may be electrically insulating, but they are advantageously conducting and held at the same potential.

It is advantageous for the insulating surfaces and the conducting surfaces extending the cylindrical surface of the external electrode to be formed by insulating and conducting annular members respectively and for the annular members to be rings or sleeves held on the external electrode by screws passing through a first conducting ring, a first insulating ring, the external electrode itself and a second insulating ring and being screwed into a second conducting ring or sleeve, the screws being insulated in relation to the external electrode but being in electric contact with the two conducting rings or sleeves.

It is advantageous for the internal electrode to extend axially beyond the first conducting ring at the opposite end from that of the centering device. The second electrically conducting ring preferably forms the frustoconical recess of the centering device.

It is, moreover, advantageous for the frustoconical contact faces of the male element and of the recess both to be electrically conducting, the surface of the recess being connected to the third terminal and that of the male element being connected to a fourth terminal. The third and fourth terminals are preferably earth terminals intended to be interconnected during operation. Advantageously they constitute protection for the second and first terminals respectively.

The coefficients of thermal expansion of the external electrode, of the material of the insulating rings and the material of the conducting rings on the one hand may be identical or nearly identical and the coefficients of thermal expansion of the internal electrode, of the male element of the centering device and of the internal electrode support on this male element on the other hand may be identical or nearly identical and also sufficiently close to the first mentioned thermal expansion coefficients that whatever the temperature variations may be during use of the cell, the mutual alignment of the internal and external electrodes is not altered.

The external electrode is advantageously subjected to thermostatic control. For this purpose, it may include circulation channels for a fluid, covered with an insulating substance so that the circulating fluid should not be in electrical contact with the external electrode.

Figure 2:
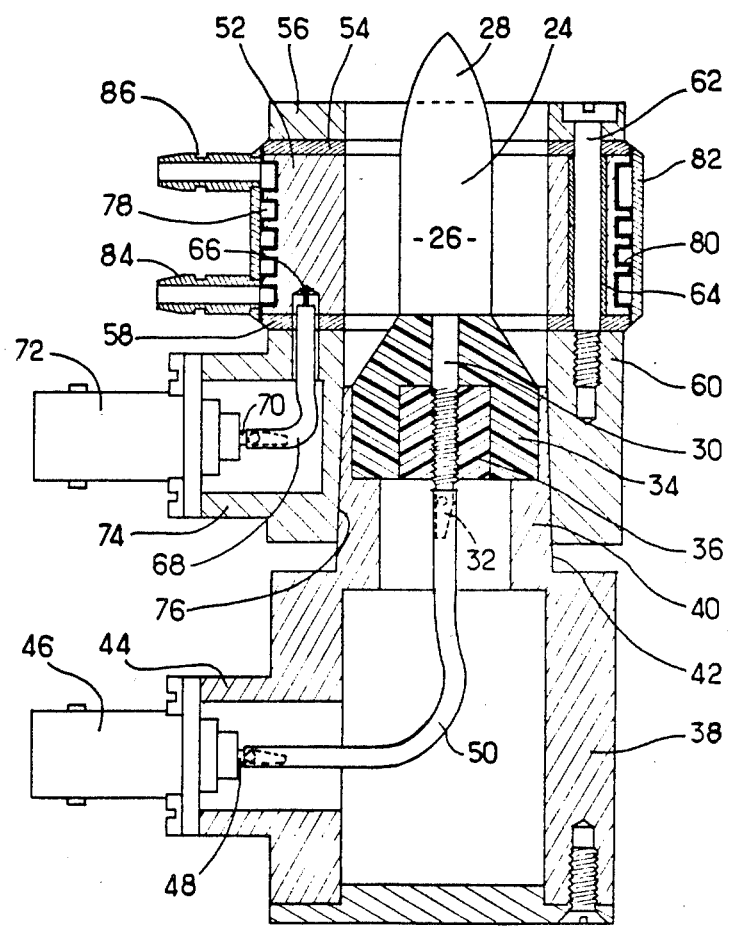

In order that the present invention may more readily be understood, there will now be described an embodiment shown on the accompanying drawings by way of a purely illustrative and non-restrictive example. In these drawings:

FIG. 1 is a simplified schematic diagram of an apparatus for the measurement of the dielectric constant of a viscous or a pasty substance; and FIG. 2 is an axial cross section of a measurement cell in accordance with the invention.

FIG. 1 shows a circuit of known type, used for measuring the dielectric constant of various substances in a cell 10 having separate terminals for the two electrodes of a capacitor device, these terminals being insulated with respect to earth. Thus the cell 10 has an earth connection 12 and two leads 14, 16 connected to the first and second electrodes of cell 10 respectively. These leads 14, 16 are joined to a capacitance meter 18 which comprises a graduated dial 20 directly indicating the capacitance in sub-multiples of farads and a device 22 for the adjustment of the measurement frequency. This capacitance meter 18 is itself earthed by wire 19.

In the example to be described, cell 10 in the circuit is to be a cell in accordance with the invention and apparatus 18 is a type 1621 "Gen-Rad" impedance bridge allowing measurements between 5 Hz and 100 Hz.

FIG. 2 shows cell 10 in detail. This cell comprises an inner electrode 24 having a cylindrical metal body part 26 extended by a bullet-shaped tip 28. Tip 28 projects outside the cell. The cylindrical body part 26 is extended at the opposite end from that of tip 28 by a rod 30 having a threaded portion and ending in a soldering lug 32. The base of the cylindrical body portion 26 and rod 30 are held by an insulating support 34 which is integral with a tapped retaining element 36. The outer surface of support 34 has a cylindrical part intended to be accommodated in a bore hole of base frame 38 and a frustoconical portion connecting the surface of the cylindrical part of support 34 to the cylindrical body portion 26 of the internal electrode. Support 34 is adjusted and held by bonding within base-frame 38, more particularly in a male element 40 of this base frame. This male element 40 has a frustoconical outer surface 42 and forms part of the centering device (according to the invention).

At its lower part on FIG. 2, base frame 38 has a projecting part 44 which itself is supporting a standard connector, for instance of the "BNC 50" type which has an outer electrically conductive or earthed part 46 and a central terminal 48 insulated in relation to the external terminal 46. An electric lead 50 is soldered on the one hand to lug 32 and on the other hand to terminal 48.

The base frame 38, the projecting part 44 and the outer part 46 of the connector are electrically conductive and are intended to be at earth potential. A second electric circuit is formed by the internal electrode 24, its rod 30, lead 50 and the insulated terminal 48; this circuit is surrounded by the base frame circuit and is thus protected against external electric interference.

The cell comprises a second element which may be separate from the first described above. This second element is essentially intended to carry an external electrode, itself intended to form a metering capacitor with the internal electrode 24 and more particularly, with its cylindrical portion 26. The external electrode 52 has an inner cylindrical surface which, in the position shown in FIG. 2 has the same axis of revolution and the same axial extent as the cylindrical body portion 26 of the internal electrode. Electrode 52 is surrounded at one end by an electrically insulating ring 54 and an electrically conductive ring 56 and at the other end by an insulating ring 58 and a conductive sleeve 60. These insulating and conductive rings and sleeve extend the cylindrical part of this external electrode.

The above mentioned insulating and conductive rings and sleeve are fixed to the external electrode 52 by means of screws 62 which pass into aligned bores of the outer conductive ring 56, of the insulating ring 54, of the external electrode 52 and of the insulating ring 58; the screws 62 are screwed into tapped holes of sleeve 60. It should be noted that a respective insulating sleeve 64 prevents all electric contact between each screw 62 and the external electrode 52. As a result, the conductive ring 56 and sleeve 60 are in electric contact with one another but remain insulated in relation to the external electrode 52.

The external electrode 52 comprises a recessed hold 66 within which is soldered one end of an electric lead 68 which is protected by an insulating sleeve and whose other end is soldered to the inner terminal 70 of a standard connector, for instance of the "BNC 50" type having an external or earthed terminal 72. This connector is screwed onto a projecting part 74 of sleeve 60.

Sleeve 60 has an inner surface 76 forming a frustoconical recess which is complementary to the frustoconical male element 40. When they are in contact, the frustoconical surfaces 42 and 76 ensure the centering of the external electrode 52 in relation to the internal electrode 24.

Channels 78 are formed peripherally of the outer surface of the external electrode 52. These may be in the form of only a single helical channel. These channels carry an electrically insulating coating 80 so that fluid circulating therein could not come into electrical contact with the external electrode 50. An external sleeve 82 encloses the channels, and end fittings 84 allow feed end discharge of a fluid. These end fittings 84 may each include a groove for the rapid attachment of circulation lines for a thermostatically controlled fluid.

Electrode 52 is connected via a first electric circuit to a central terminal 70 of the connector 72 whose earth terminal is in contact with the guard sleeve 60 and, via the screws 62, with the guard ring 56. The conductive ring 56 and sleeve 60 are placed very close to the external electrode 52 and extend the inner surface thereof. The electric field lines between the cylindrical portion 26 of the internal electrode 24 and the external electrode 52, are substantially perpendicular to the axis of revolution of these cylindrical portions. The electric field lines are only curved at the level of the guard ring 56 and sleeve 60 and cannot therefore interfere with the measurement which is effected between the cylindrical portions 26 and 52. It should be noted that the tip 28 of the internal electrode 24 projects beyond the guard ring 56 and this arrangement facilitates the distancing of the curved electric field lines in relation to the cylindrical portions 26 and 52.

It should be noted that the conductive parts of the two elements are advantageously formed of an inert substance with very good electric and thermal conductivities such as a noble copper alloy covered with a protective nickel plating. The insulating elements are advantageously formed of a ceramic whose expansion coefficient is similar to that of the electrically conductive components. In this way, the relative position of the two electrodes is not modified in cases of temperature variation.

It will be noted that the two separable elements of the cell 10 define an annular cylindrical housing intended to contain the substance to be measured. This housing is a body of revolution and has smooth and regular surfaces. Thus on the first element, that is to say, the one carrying the internal electrode 24, the surface gradually widens as far as the base frame 38 and it can be very easily cleaned in view of its shape of revolution. Similarly, the second element carrying the external electrode 52 simply comprises a substantially cylindrical cavity extended by a frustoconical cavity so much so that cleaning is also very convenient.

Another advantage of the cell in accordance with the invention is that the centering ensured by the frustoconical surfaces 42 and 76 is accurately reproducible. In this way, the axes of revolution of the cylindrical portion 26 of the internal electrode and of the external electrode 52 are always identical; moreover, their relative axial position is always the same, so much so that the cylindrical parts always face each other.

Finally, the lower sleeve 60 and the co-operating male element 40 are both electrically conducting but they are both earthed by means of the external terminals of the bayonet connectors 46 and 72 or by additional conductive terminals. In this way, even if a film of the substance to be measured remains between the two frustoconical contact surfaces 42 and 76, the measured value is not interfered with by the more, or less efficient current flow at the level of this interface. Moreover, the reliability of the measurements is ensured by using contacts which are soldered to the two electrodes.

Thus, dismantling, cleaning and reassembly of the cell are easy. The electrodes 24 and 52 always reassume the same geometrical disposition, and this does not vary when there are variations in temperature. Filling the cell does not in any way modify the position of the electrodes, which are very robust. The cavity containing the liquid to be measured has a small volume, so much so that the quantity of the substance necessary for the measurement is small. Given the nature of the various cell devices, they do not react with the liquids and pastes whose properties are being measured and thus have great inertia. Moreover, these cells are not corroded by the liquids which may be measured. Furthermore, the terminals are protected by earthing.

The apparatus described allows the dielectric properties of pure or mixed substances to be measured in a liquid, pasty or even a solid state when the melting temperature is sufficiently low for the material to be poured into the cell. Thus the cell is suitable for measuring the electric properties of waxes, greases and similar substances. These measurements may be effected over a whole range of temperatures, for instance between 20° and 80° C. thanks to the thermostatic regulation of the temperature of the external electrode.

The cell 10 may be used, for instance, for measuring the purity of a product such as for example, a pharmaceutical product; for studying the behaviour of dielectric substances in the electronic and electrical engineering industries; for measuring the dissipation of emulsions and compounds, particularly in cosmetics or in the oil industry; and, generally speaking, for all checks of the electric behaviour of liquid, viscous or pasty substances related to the applied frequency.

It shall be duly understood that the invention has only been described and represented by way of a preferred example and that any technological equivalent may be applied to its constituent elements without thereby departing from its scope as defined by the following claims. Thus, in a variant, the internal electrode 24 could also be provided with guard rings formed by the mounting of elements on rod 30; in this latter case, it would not be indispensable for the internal electrode 24 to project axially beyond the element comprising the external electrode 52.

We claim:

1. In a cell for the measurement of the dielectric properties of a viscous or pasty substance comprising: first and second separable elements, said first separable element having an outer cylindrical electrically conductive surface and forming an internal electrode and said second separable element having an inner cylindrical electrically conductive surface and forming an external electrode; a first terminal connected to said first separable element; a second terminal connected to said second separable element; and centering means to keep said first and second separable elements in cooperation with each other in an operating position wherein said inner and outer cylindrical electrically conductive surfaces are substantially coaxial and are at least partly disposed opposite each other; the improvement comprising: (a) inner cylindrical surface means extending said inner cylindrical surface of the external electrode at each one of its ends, said inner cylindrical surface means comprising means defining an electrically insulating surface adjacent to said inner cylindrical surface of the external electrode and also an electrically conductive cylindrical surface therebeyond, the said electrically conducting inner surfaces of the inner surface means being insulated in relation to the external electrode; (b) a third terminal electrically connected to both of said electrically conductive inner surfaces of the inner surface means; (c) a frustoconical male element of said centering means, formed on said first element and having the same axis of revolution as said internal electrode thereof; and (d) a frustoconical female element of said centering means, formed in said second element and having the same axis of revolution as the external electrode thereof, said male and female elements of said centering means having respective frustoconoical surfaces which are both electrically conductive and said third terminal comprising an electrical conductor connected to the conductive surfaces of said first element and a separate electrical conductor connected to the conductive surface of said second element whereby said conductive surfaces of said first and second elements may be connected to a potential ground, said first element having a base with said male element being formed on said base and insulating means being disposed between said internal electrode and said male element.

2. A cell according to claim 1, wherein said inner cylindrical surface means are formed by first and second electrically insulating annular members and first and second electrically conductive annular members; including screw means holding said annular members held on the external electrode, said screw means passing through said first electrically conductive annular member, said first electrically insulating annular member, the external electrode and said second electrically insulating annular member, and including means electrically insulating said screw means in relation to the external electrode and means electrically contacting said screw means with said first and second electrically conducting annular members.

3. A cell according to claim 2, wherein said internal electrode has first and second ends with said centering means at said first end, and wherein said second end of said internal electrode projects beyond said first electrically conductive annular member.

4. A cell according to claim 2, wherein said second electrically conductive annular member forms said female element of the centering means.

5. A cell according to claim 1, wherein said third and fourth terminals are earth terminals to be interconnected during operation of said cell.

6. A cell according to claim 5, wherein said third and fourth terminals form means protecting the second and first terminals respectively.

7. A cell according to claim 2, wherein the external electrode has a first thermal expansion coefficient, the material of the first and second electrically insulating annular members has a second thermal expansion coefficient, the material of the first and second electrically conductive annular members has a third thermal expansion coefficient, the internal electrode has a fourth thermal expansion coefficient, the male element of the centering means has a fifth thermal expansion coefficient, and the internal electrode is mounted on said male element by means having a sixth thermal expansion coefficient; and wherein said first, second and third thermal expansion coefficients are sufficiently close to said fourth, fifth and sixth thermal expansion coefficients for the relative positioning of the internal and external electrodes not to be substantially modified by variations in temperature.

8. A cell according to claim 7, wherein at least two of said first, second and third thermal expansion coefficients are identical.

9. A cell according to claim 7, wherein at least two of said fourth, fifth and sixth thermal expansion coefficients are identical.

10. A cell according to claim 1, including means thermostatically controlling said external electrode.

11. A cell according to claim 10, wherein said thermostatically controlling means comprises fluid circulation conduits of the external electrode for the circulation of a fluid in heat-conducting relation therewith, and means electrically insulating a fluid in said fluid circulation conduits from said external electrode.

* * * * *